US007191803B2

(12) United States Patent
Orr et al.

(10) Patent No.: US 7,191,803 B2
(45) Date of Patent: *Mar. 20, 2007

(54) ELASTIC FABRIC WITH SINUSOIDALLY DISPOSED WIRES

(75) Inventors: Lawrence William Orr, Simpsonville, SC (US); Helen Beaman, Simpsonville, SC (US); Bob Weeks, Pelzer, SC (US); Gloria Grandison, Liberty, SC (US); Katie Richards Hammett, Piedmont, SC (US); Connie Barnett, Pelzer, SC (US); Lynn Lozynski, Wellford, SC (US)

(73) Assignee: Woven Electronics Corporation, Simpsonville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/235,470

(22) Filed: Sep. 26, 2005

(65) Prior Publication Data

US 2006/0124193 A1    Jun. 15, 2006

Related U.S. Application Data

(60) Provisional application No. 60/635,496, filed on Dec. 13, 2004.

(51) Int. Cl.
   *D03D 11/00*   (2006.01)
   *D03D 11/02*   (2006.01)
   *A41D 27/02*   (2006.01)
   *A41D 27/00*   (2006.01)
(52) U.S. Cl. .................. 139/421; 139/408; 139/420 R; 139/422; 139/423; 139/425 R; 139/426 R; 2/258; 2/272; 2/905

(58) Field of Classification Search ................. 139/408, 139/420 R, 421, 422, 423, 425 R, 426 R
See application file for complete search history.

(56) References Cited

U.S. PATENT DOCUMENTS

| 857,367 | A |   | 6/1907 | Shore |
|---|---|---|---|---|
| 2,327,756 | A | * | 8/1943 | Adamson ..................... 219/545 |
| 2,831,235 | A | * | 4/1958 | Schuyler ...................... 28/155 |
| 3,479,565 | A |   | 11/1969 | Ross et al. |
| 3,711,627 | A | * | 1/1973 | Maringulov ................. 174/255 |
| 4,577,256 | A | * | 3/1986 | Breidegam .................. 361/220 |
| 4,654,748 | A | * | 3/1987 | Rees .......................... 361/220 |
| 4,664,158 | A |   | 5/1987 | Sands |
| 4,746,769 | A |   | 5/1988 | Piper |

(Continued)

*Primary Examiner*—Robert H Muromoto
(74) *Attorney, Agent, or Firm*—McNair Law Firm, P.A.

(57) ABSTRACT

A fabric for use with a system for monitoring prescribed body functions comprising an elastic fabric, adapted to be carried by a torso, which is stretchable in its longitudinal direction so as to expand and contract in response to body movement and size. The carrier includes at least one conductive and inelastic yarn arranged longitudinally of and located between upper and lower surfaces. The conductive yarn is arranged in sinusoidal configurations longitudinally of the fabric. The conductive yarn forms a breakout through one of the outer surfaces, at selected locations along the length of the fabric, forming opposed exposed ends above the surface. A monitoring unit, which includes a connector and a sensor, is secured with the one surface at the breakout with the connector being united with the exposed ends of the conductive yarn. The fabric acts to maintain the monitoring unit in a desired stationary position allowing the sensor to sense signals emitted from the torso and transmit these senses signals.

30 Claims, 9 Drawing Sheets

U.S. PATENT DOCUMENTS

| | | | | |
|---|---|---|---|---|
| 4,813,459 A | * | 3/1989 | Breidegam | 139/421 |
| 5,823,232 A | * | 10/1998 | Georgii | 139/383 R |
| 6,210,771 B1 | * | 4/2001 | Post et al. | 428/100 |
| 6,289,939 B1 | * | 9/2001 | Mortensen et al. | 139/22 |
| 6,305,432 B1 | * | 10/2001 | Sacks et al. | 139/425 R |
| 6,341,504 B1 | * | 1/2002 | Istook | 66/172 E |
| 6,581,212 B1 | * | 6/2003 | Andresen | 2/167 |

* cited by examiner

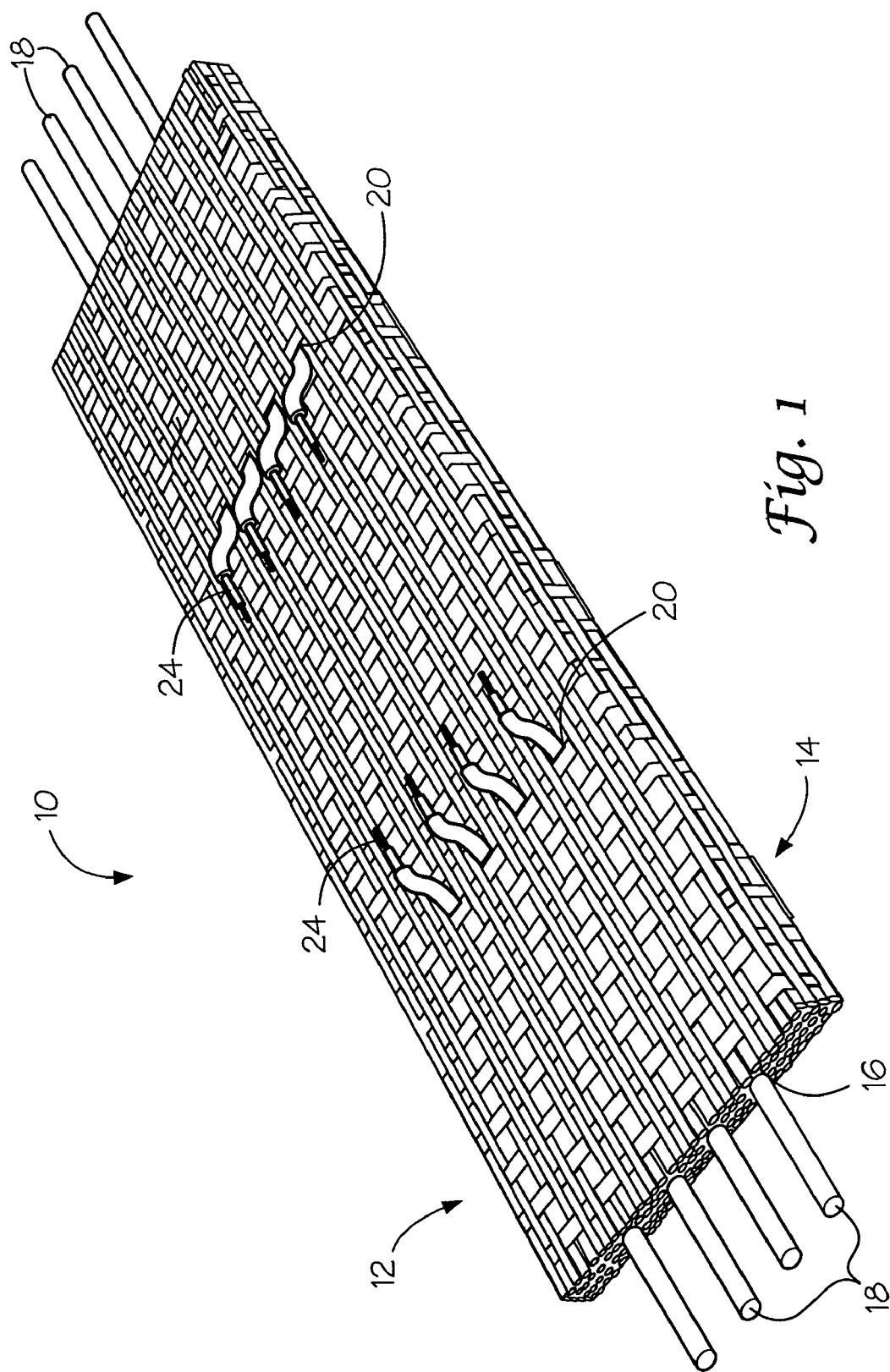

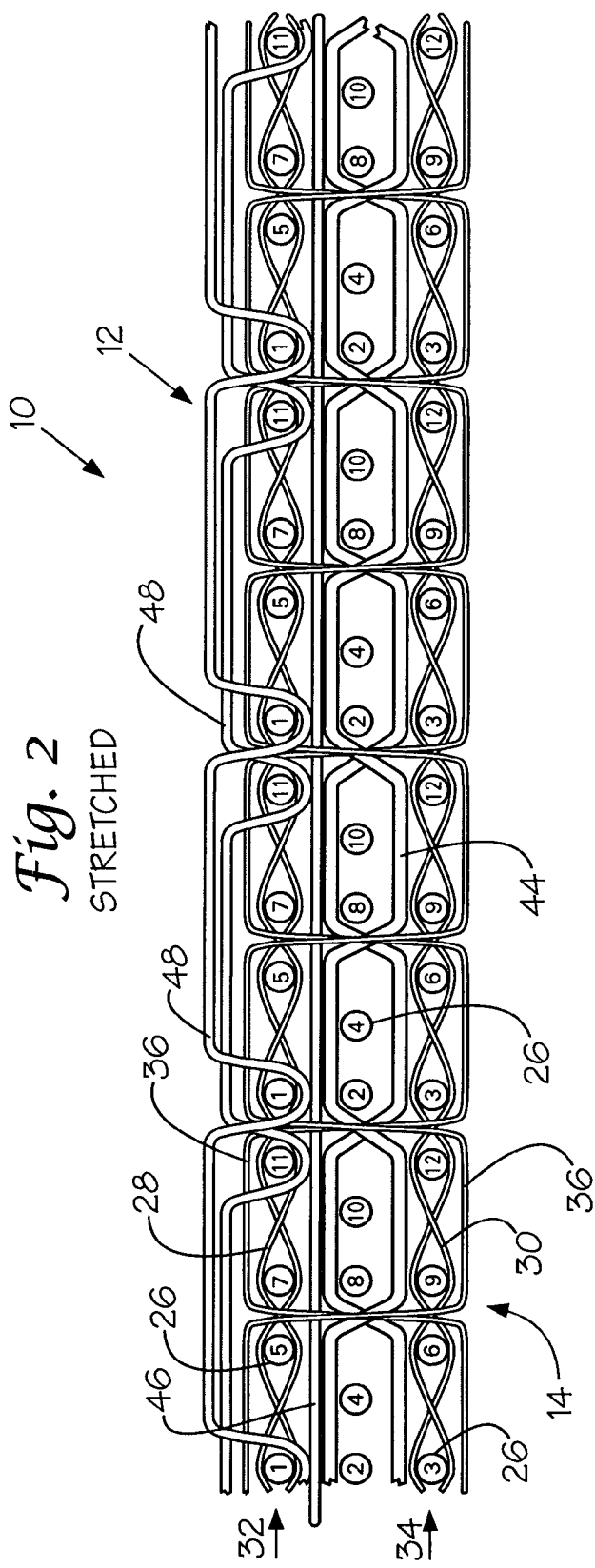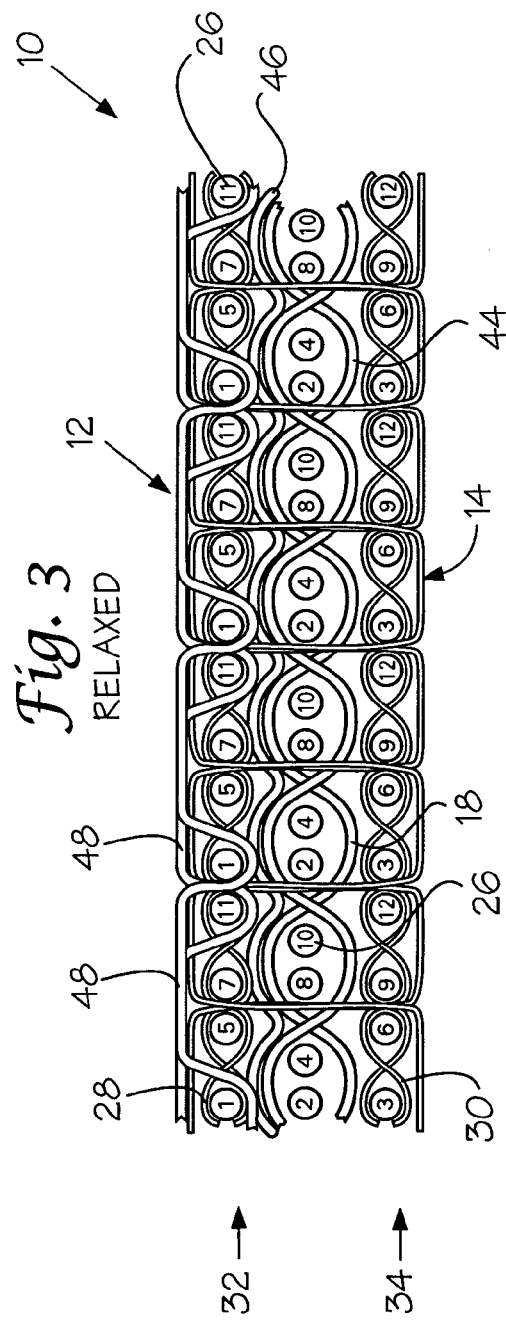

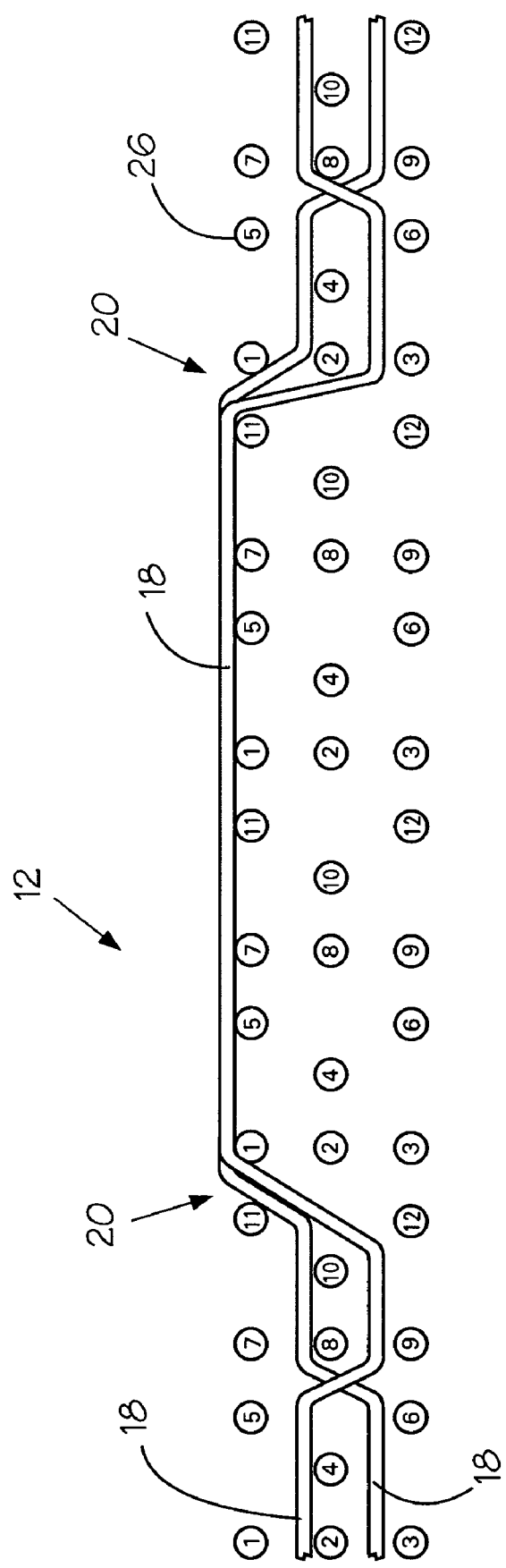

ically extending groups of laterally spaced warp yarns. A plurality of picks of inelastic weft yarn are woven into the fabric. First ones of the picks weave with the upper or lower warp yarns forming upper and lower outer surfaces of cells. A plurality of conductive warp yarns are arranged longitudinally of the fabric in controlled sinusoidal configurations in each of the cells. Second ones of the plurality of picks weave with the conductive warp yarns between the upper and lower outer surfaces positioning each of the conductive yarns in controlled sinusoidal configurations. The fabric may be extended longitudinally between 25 and 50% from its retracted position into various elongated positions causing the controlled sinusoidal configurations of the conductive yarns to be altered consistent with the degree of extension.
ELASTIC FABRIC WITH SINUSOIDALLY DISPOSED WIRES

CROSS REFERENCE TO RELATED APPLICATION

This application claims priority from a provisional application filed Dec. 13, 2004, under Application Ser. No. 60/635,496 having the same title.

BACKGROUND OF THE INVENTION

The present invention is directed to woven elastic fabrics which include one or more conductive wires and which are designed to carry systems which monitor selected prescribed body functions.

Elastic fabrics designated to carry monitoring devices are known in the art, as illustrated by U.S. Pat. No. 6,551,252. In this patent, there is only one disclosed fabric, i.e. a warp knitted fabric. The patent states that any of all fabric forming modes may be utilized, however, only one is described.

The primary drawback to a knit fabric, as above referred to, is that the conductive yarns can be controlled to lie in only a single fabric plane.

In fabrics used for carrying and positioning body function monitoring equipment it is most desirable and accordingly an object of the invention that the fabric be elastic yet be sufficiently resilient to allow it to be positioned stationarily in a selected position.

Another object of this invention is the provision of a fabric which can be elongated and retracted while maintaining its pre-set position.

Another object of the invention is an elastic fabric which carries conductive yarns in a protected inner fabric plane but brings the conductive yarns through an outer fabric surface at selected points for engagement with monitoring equipment.

Another object of the invention is the provision of an elastic fabric with a soft fleece-like surface for contact with the body exterior.

Another object of the invention is the provision of an elastic fabric which contains conductive yarns retained in adjustable sinusoidal configurations within longitudinally extending inner cells of the fabric.

Another object of the invention is an elastic fabric which controls the formation of conductive yarn loops on an outer fabric surface at selected longitudinal intervals.

Another object of the invention is an elastic fabric carrying a monitoring system for sensing signals emitted by a body.

Another object of the invention is a carrier system for securing a sensor with an elastic fabric and with conductive wires carried by that system.

SUMMARY OF THE INVENTION

The invention is directed to a carrier fabric for a sensing system for monitoring selected body functions. The fabric comprises an elastic multi-ply woven fabric which is stretchable from a retracted position into a plurality of elongated positions. The fabric comprises of a plurality of upper and lower elastic warp yarns which are arranged in vertically spaced positions forming a plurality of longitudinally extending groups of laterally spaced warp yarns. A plurality of picks of inelastic weft yarn are woven into the fabric. First ones of the picks weave with the upper or lower warp yarns forming upper and lower outer surfaces of cells. A plurality of conductive warp yarns are arranged longitudinally of the fabric in controlled sinusoidal configurations in each of the cells. Second ones of the plurality of picks weave with the conductive warp yarns between the upper and lower outer surfaces positioning each of the conductive yarns in controlled sinusoidal configurations. The fabric may be extended longitudinally between 25 and 50% from its retracted position into various elongated positions causing the controlled sinusoidal configurations of the conductive yarns to be altered consistent with the degree of extension.

The elastic warp yarns may comprise a spandex core wrapped with an inelastic textured polyester cover. The core may comprise a spandex monofilament of about 420 denier. The cover may comprise a plurality of multi-filament yarns wrapped about the core.

Conductive yarns, along with the elastic warp yarns, are controlled to form a plurality of breakout points where the conductive yarns extend through, over a selected length and back through an outer surface of the fabric. The conductive yarns individually form connector loops over the selected length of the outer surface. The connecter loops are arranged in transverse rows across the fabric and are formed at selected longitudinal locations.

The fabric is woven in a twelve pick repeating pattern and is formed with anywhere between one and twelve conductive warp yarns. The conductive warp yarns are individually located in the cells.

The conductive warp yarn comprises a wire filament core covered with wrapped textured or non-textured synthetic yarns.

The fabric includes a plurality of elastic edge warp yarns which weave with the second ones of the picks which also weave with the second ones of the picks which also weave with the conductive warp yarns.

The fabric also includes elastic binder warp yarns which are arranged to weave between adjacent of the cells with selected of the picks to longitudinally separate the cells.

The selected picks weaving with the conductive yarns act to bend the conductive yarns in vertical directions creating first ones of the controlled sinusoidal configurations in the conductive yarns which configurations extend generally along a vertical plane and form the controlled sinusoidal configurations.

There are also provided elastic stuffer yarns which extend longitudinally of the fabric, within each of the cells, on opposite sides of each of the conductive yarns. The stuffer yarns act to stabilize the conductive yarns within the cells.

A method of forming a length of multi-ply elastic fabric for use in a sensing system which includes:

(A) Causing a plurality of elastic warp yarns to be elongated along first and second vertically spaced planes in a plurality of laterally spaced positions and weaving selected picks of a plurality of picks with the selected warp yarns to form upper and lower surfaces for a plurality of cells;

(B) Causing a plurality of conductive yarns to extend along the cells between the upper and lower surfaces;

(C) Weaving selected other picks, of the plurality of picks, with the conductive warp yarns shaping the conductive warp yarns into controlled sinusoidal configurations within the cells;

(D) Causing the elongated elastic warp yarns to contract reducing the fabric length, causing the sinusoidal configurations to assume enlarged sinusoidal shapes between the upper and lower surfaces while the upper and lower surfaces formed of the elastic warp yarns maintain the controlled sinusoidal shapes and the conductive warp yarns to remain within the cells.

The method also includes causing the conductive yarns to extend through or breakout through an outer surface at selected longitudinal points along the fabric length to form loops over the outer surface. The breakout points forming connecting points for connecting the conductive yarns with a monitoring system.

A multi-ply carrier fabric for use in a physiological sensing system which includes first, second and third elastic warp yarn groups each interwoven with selected ones of a plurality of picks of inelastic weft yarn through a weave pattern. The formed fabric includes a plurality of longitudinally extending individual cells.

A first warp yarn group is controlled to weave with first ones of the picks forming an upper layer of the cells. A second warp yarn group which has fewer warp yarns than the first warp yarn group is controlled to weave with second ones of the picks forming a lower layer of the cells. A third warp yarn group is arranged between the first and second warp yarn groups and is controlled to weave with each pick of the plurality of picks binding the upper and lower layers together and completing the formation of the cells.

An inelastic conductive yarn is arranged to extend within each cell along a sinusoidal path. Certain warp yarns of the first warp yarn group are textured providing the upper layer with a textured or plush feel.

Selected of the picks of weft yarn weave with the conductive yarns within the cells. These picks act to shape the conductive yarns into first ones of the sinusoidal shapes. At the breakout points, where the conductive yarns form loops above the upper layer of the fabric, these picks simply float through the cells.

A system for monitoring prescribed body functions which comprise a carrier worn over a portion of a torso, which includes a composite elastic fabric stretchable in its longitudinal direction so as to expand and contract in response to body movement and size. The carrier includes at least one conductive and inelastic yarn located between outer upper and lower fabric surfaces which is positioned in sinusoidal configurations longitudinally of the fabric. There is provided a breakout of the conductive yarn through an outer surface where opposed and exposed ends of the conductive yarns are arranged in opposed positions. A monitoring unit, which includes a connector and a sensor, is secured with the outer surface at the breakout, where the connector is united with the exposed ends of the conductive yarns. The fabric functions to maintain the monitoring unit in a desired stationary position to sense signals emitted from the torso and to transmit these sensed signals to a receiver.

The monitoring unit includes a PC board secured adjacent the surface of the fabric. The PC board includes exposed contacts which are adapted to secure with the exposed ends of the conductive yarns. An insulating pad is positioned between the outer surface and the PC board. The monitoring unit also includes a mounting cap which is adapted to releasably support the monitor. The mounting cap includes engaging members which are adapted to secure with the elastic fabric to lock the mounting cap in position adjacent the surface of the elastic fabric.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein:

FIG. 1 is a perspective view of the elastic carrier fabric of the invention.

FIG. 2 is a cutaway side view of the weave of the carrier fabric in an elongated condition.

FIG. 3 is a cutaway side view of the fabric of FIG. 2 in its relaxed condition.

FIG. 4 is a sectional cutaway end view showing the relationship of the conductive warp yarn at a breakout point with the picks of weft yarn.

DESCRIPTION OF A PREFERRED EMBODIMENT

Figure 5:
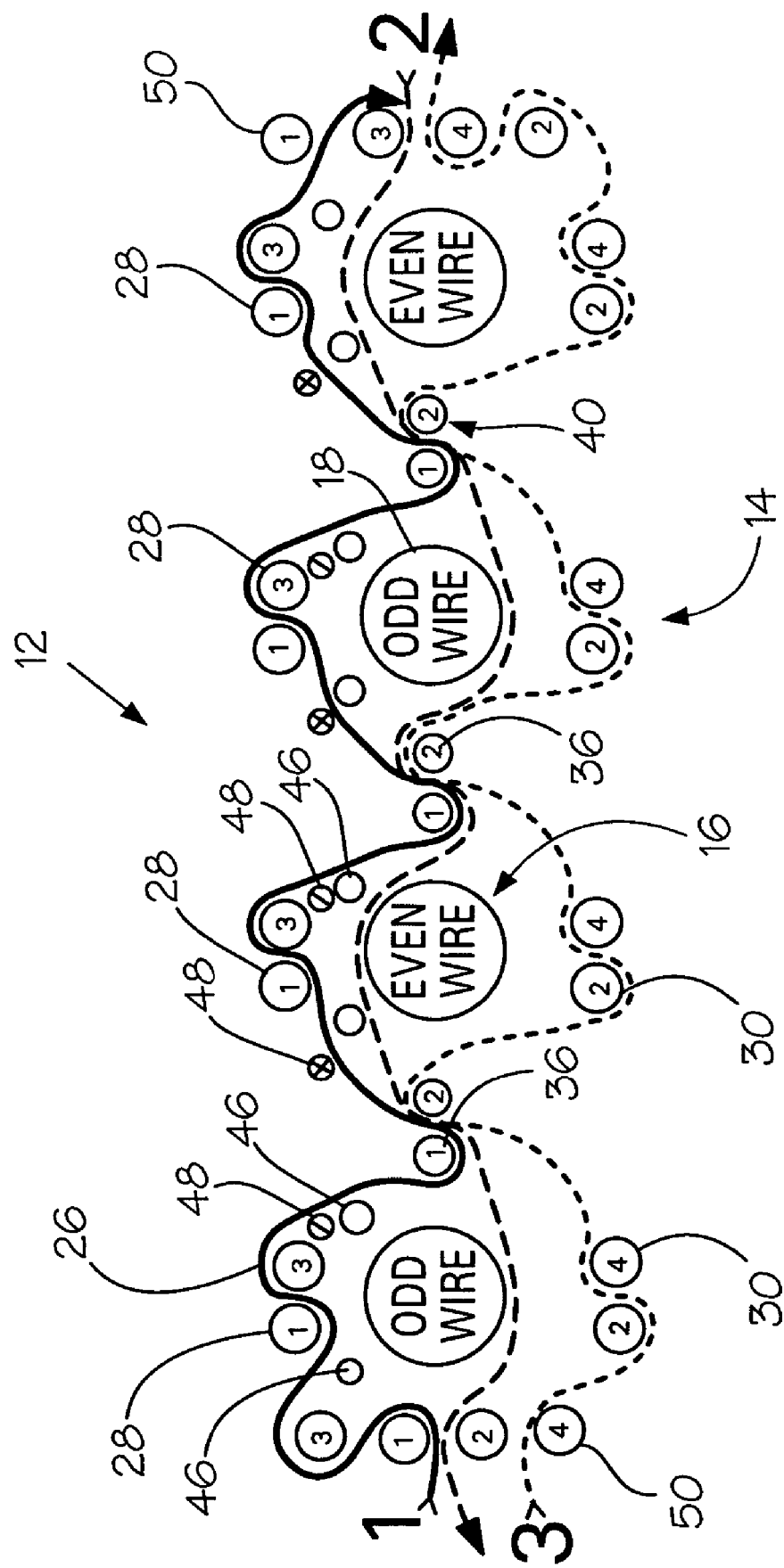
FIG. 5 is a cutaway end view showing picks 1–3 of the weft yarn.

Systems have now been developed which are capable of sensing and transmitting data from a person's body during activity. The systems are adapted to individually monitor respiration, pulse rate, skin temperature and blood pressure. The instant invention is directed to the structure of a carrier fabric which, when fitted onto a person's body, acts to remain as positioned, is capable of expanding and contracting and possess antenna capable of transmitting collected data. It is also desired that the carrier fabric be as non-intrusive as possible. The invention also includes a carrier which connects with the carrier fabric and individually with the conductive yarns of the fabric. The carrier carries a monitor in engagement with the conductive yarns.

Turning now to FIG. 1 of the drawing, there is shown a section of carrier fabric 10 of the invention. Fabric 10 is a multi-ply fabric having an upper surface 12 and a lower surface 14. Fabric 10 includes a plurality of longitudinally extending cells 16, each of which contains a conductive warp yarn 18. The conductive yarns 18 extend along the fabric length within the cells shielded or encased by the upper and lower surfaces 12 and 14.

At selected points along the fabric length, conductive yarn 18 is caused to breakout of the inner fabric area as shown at 20 and form loops over the outer surface. Loops 22, as shown in FIG. 4, are cut, leaving exposed ends 24 arranged in opposed positions.

Figure 6:
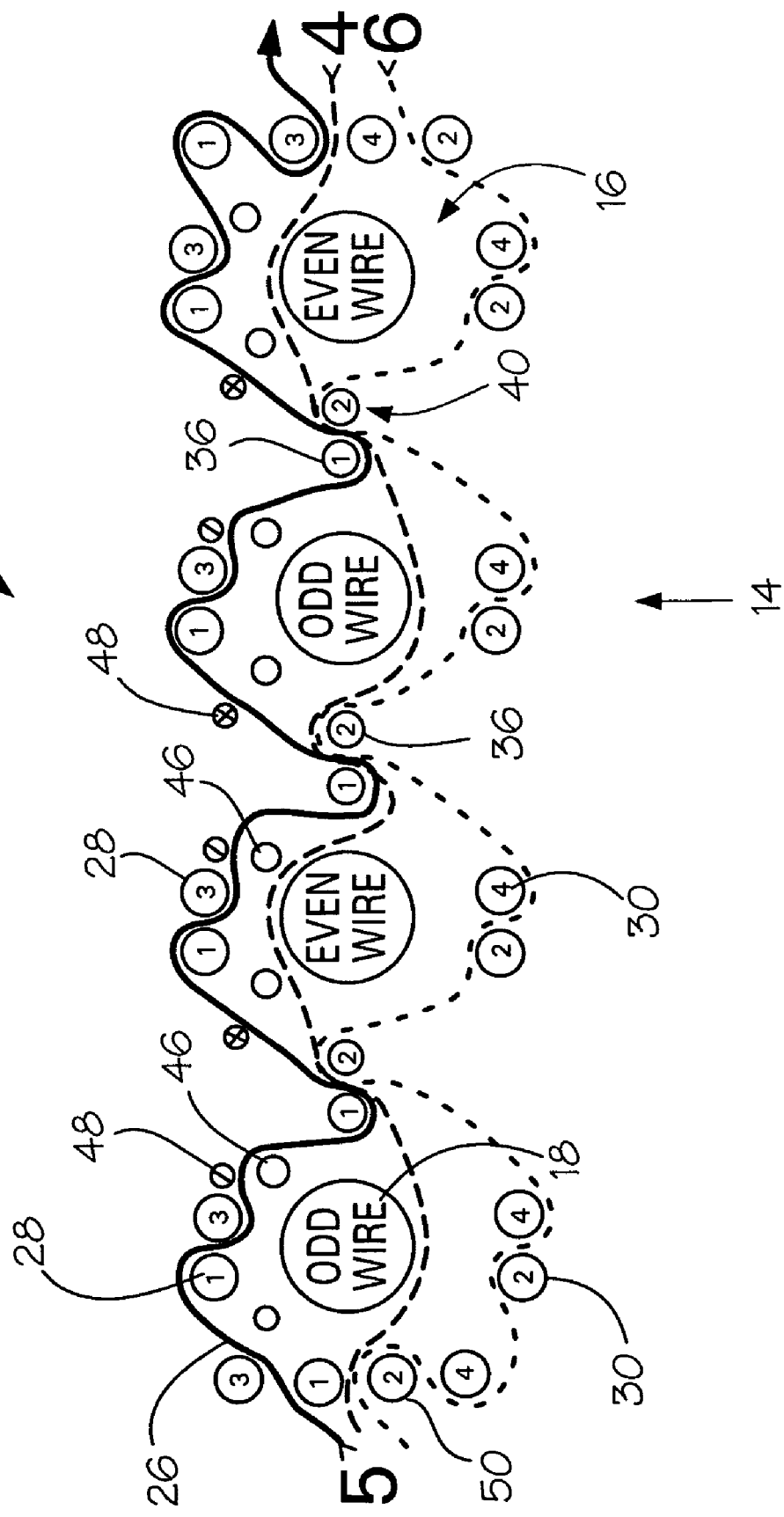
FIG. 6 is similar to FIG. 5 showing picks 4–6 of the weft yarn.
Figure 7:
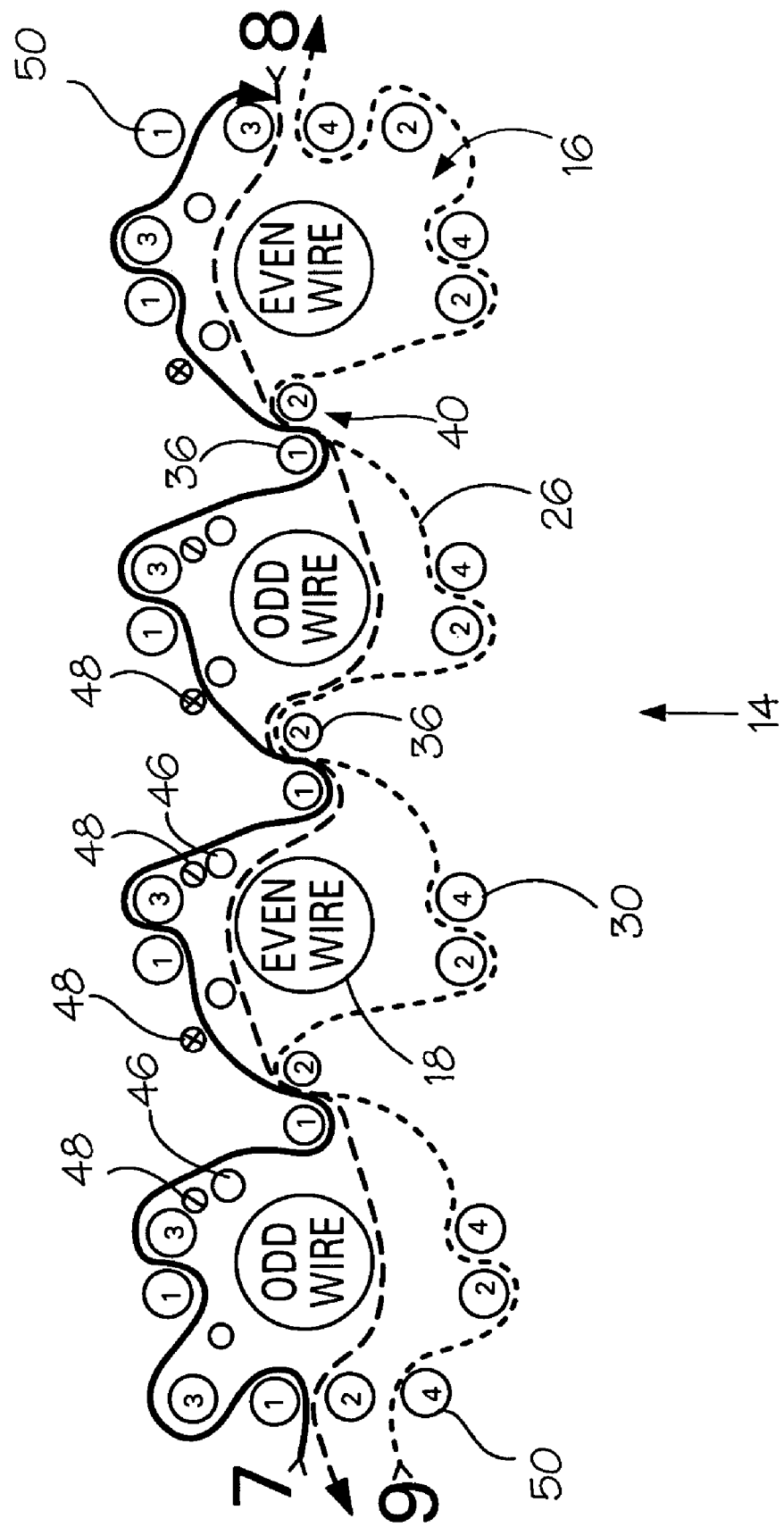
FIG. 7 is similar to FIG. 5 showing picks 7–9 of the weft yarn.
Figure 8:
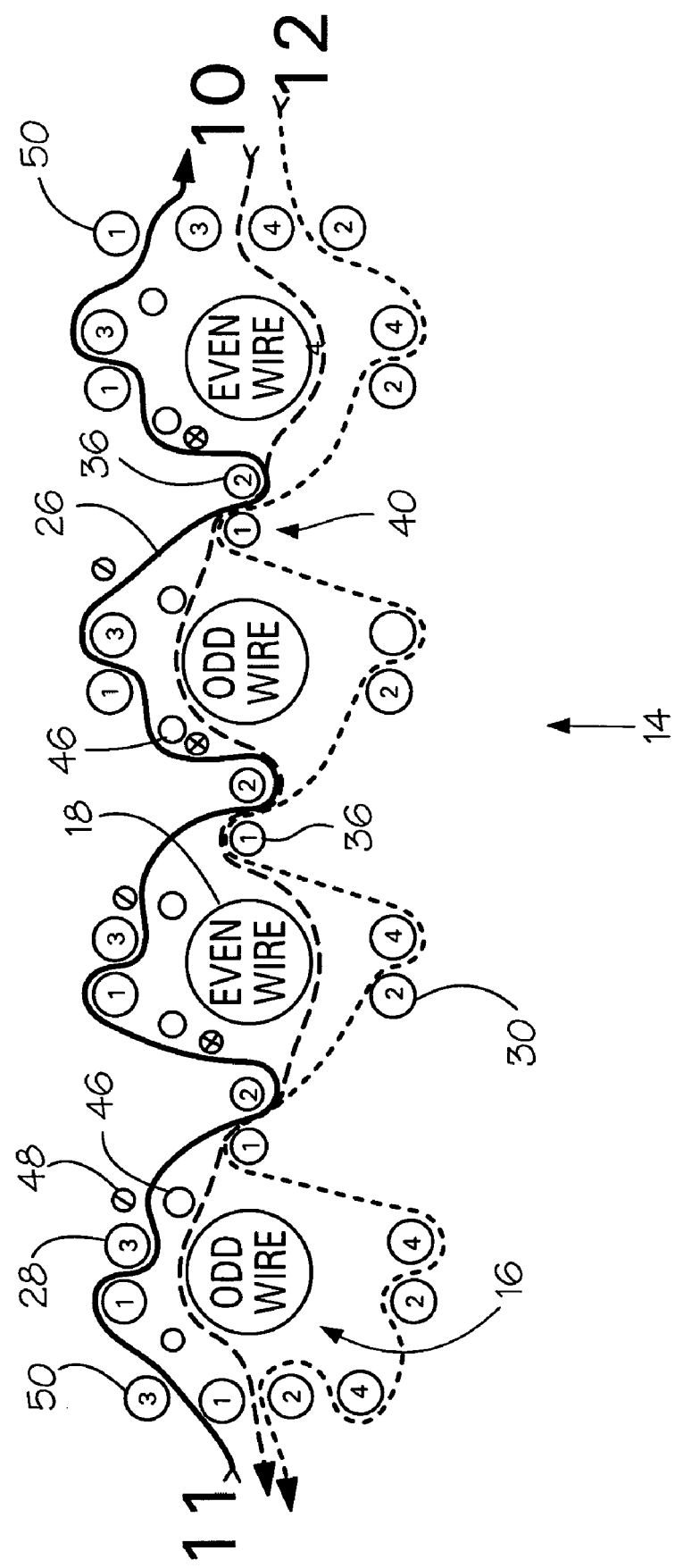
FIG. 8 is similar to FIG. 5 showing picks 10–12 of the weft yarn.
Figure 9:
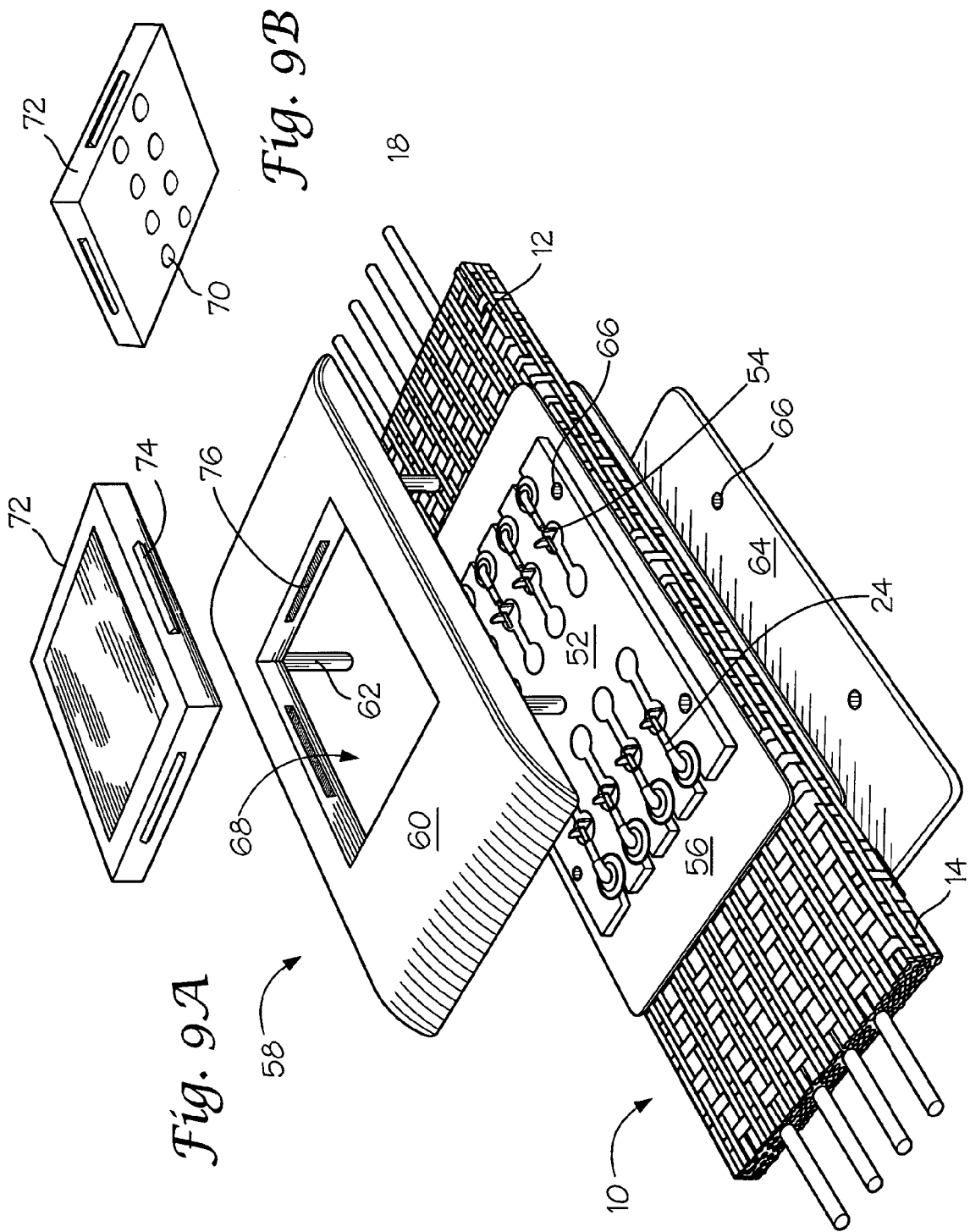
FIG. 9A is an exploded perspective view showing the sensing device engaged with the carrier fabric and the conductive yarns.
FIG. 9B is a perspective view of the underside of the sensing element.
Figure 10:
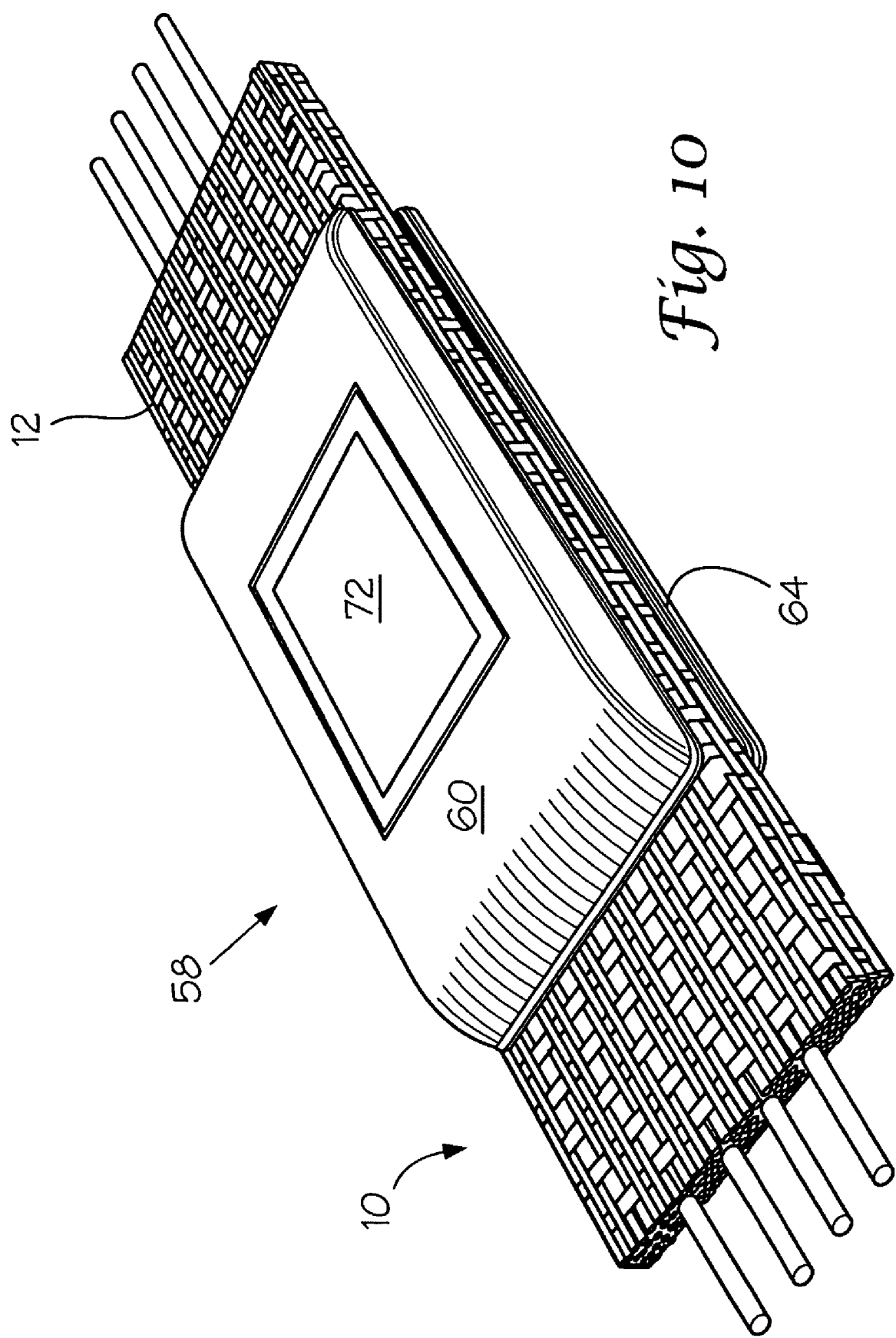
FIG. 10 is a perspective view of the sensing device in position on the carrier fabric.

Fabric 10, as best shown in FIGS. 2–8, is woven in a twelve pick weave pattern utilizing an inelastic weft yarn 26. The picks are sequentially numbered 1–12. The elastic warp yarns are arranged in a plurality of groups with warp yarns 28 and 30 being arranged in upper and lower groups of two yarns, which are vertically disposed. As shown in FIGS. 2 and 5–8, warp yarns 28 weave only with picks 1 and 5 in an upper plane while warp yarns 30 weave only with picks 3 and 6. This weave pattern creates an upper ply 32 and a lower ply 34, which are vertically separated and extend longitudinally of the fabric. Warp yarns 36 are arranged between the adjacent upper and lower groups of warp yarn 28, 30 and weave with all weft picks 1–12, forming binder strips 40 which act to bind upper and lower plys 32, 34 together forming a plurality of cells 16 across the width of the fabric.

A conductive yarn 18 is positioned within each cell 16 to extend longitudinally of the fabric. Conductive yarn 18 preferably comprises a metallic filament of between 25 and 30 gauge, coated with a latex or rubber cover. It is preferred that the metallic filament be about 28 gauge. As best shown in FIGS. 2–4, conductive yarns 18 are woven with picks 2, 4, 8 and 10 of weft yarn 26, which causes crimps or bends in each conductive yarn or the conductive yarns are shaped into controlled sinusoidal configurations along the length of the fabrics as clearly shown in FIGS. 2 and 3.

In order to control the lateral position of the conductive yarns 18 within each cell 16, a pair of stuffer yarns 46 are positioned above and adjacent opposed sides of each conductive yarn 44 as clearly shown in FIGS. 2, 3, 5–8. The stuffer yarns do not weave with weft yarn 26 but simply float through the cell.

In order to provide a soft or fluffy feel on the outer surface which is intended to engage with the body, cover yarns 48 are interwoven with picks 1, 5, 7 and 11 of upper surface 12 in a three-up, one-down twill weave or any selected weave pattern.

As is usual when weaving elastic fabrics, the elastic yarns are put under tension and are elongated during formation of the fabric as is shown in FIG. 2. As the fabric comes off the loom, it contracts as shown in FIG. 3. In this condition, the picks are drawn closer together as the elastic yarns contract. The sinusoidal configurations of the conductive yarns are forced into enlarged but controlled sinusoidal configurations during and after contraction. Because conductive yarns 18 are interwoven with the fabric within cells 16 by picks 2, 4, 8 and 10, they are maintained in position relative to the fabric length. This results in only an upward and downward motion of the conductive yarns as the size and shape of the sinusoidal configurations are adjusted relative to the fabric length.

In order for fabric 10 to effectively function as a carrier fabric for a monitoring system, breakouts 20 which are formed at selected locations along the fabric length. A breakout is where conductive yarns are brought through upper surface 12 to extend over a length of fabric before being moved back into their respective cell. The manner in which yarns 18 are controlled at a breakout is shown in FIG. 4. The breakout length is controlled over a weave pattern repeat. At the end of a selected weave pattern, which involves picks 10, 11 and 12, conductive yarns 18 are brought above upper surface 12 to float for a selected distance, usually only one repeat of the weave pattern. All other warp yarns weave as earlier described with picks 1–12 of the weft yarn. Picks 2, 4, 8 and 10 weave with warp 36 forming the binder between the cells. These picks simply float across the cells.

There are provided edge warp yarns 50, best shown in FIGS. 5–8, which weave with all picks 1–12 of weft yarn 26 closing of finishing the outer edge of the fabric.

Yarn Index

The preferred yarns forming the disclosed fabric are:
Weft yarn preferably non-elastic textured polyester 2/200/96;
Warp rubber preferably 32–32 gauge;
Warp elastic textured preferably 840 denier nylon;
Cover or center warp preferably 2/200/96 polyester;
Conductive preferably 24 gauge;

With fabric 10 is formed to desired length and with loops 22 formed at selected locations, each loop is cut and opposed ends of each conductive yarn 18, are stripped leaving exposed ends 24 as shown in FIG. 1. PC board 52 is positioned on surface 12 of the fabric in position for stripped ends 24 to be engaged with contacts 54. Preferably, an insulating pad 56 is positioned between surface 12 and board 52. A securing member 58, is attached to both PC board 52 & fabric 10, locking the PC board in position.

In the instant arrangement, securing member 58 comprises an upper plate 60 with a plurality of pegs 62 extending from its lower surface. Lower plate 64 is positioned against lower surface 14 of fabric 10 and includes openings 66, which are adapted to receive pegs 62 of upper plate 60. To lock the PC board with surface 12 of the fabric, pegs 62 are passed through the openings in the PC board, through fabric 12 and are secured in openings 66 of lower plate 64. This locks the carrier with fabric 12 with PC board 52 interconnected with conductive yarns 18.

Upper plate 60 includes central opening 68, which is adapted to releasably receive and secure monitor 72 in position to engage with PC board 52. Monitor 72 includes contacts 70 on its lower surface which are positioned to engage with contacts 54 of PC board 52 connecting monitor 72 with conductive yarns 44. Retractable snaps 74 of usual construction are pressure fit with grooves 76 to maintain monitor 72 in position relative PC board 52. Other known releasable engagement structures may be utilized if desired to releasably position the monitor within opening 68.

In use fabric 10, arranged as a circular band, is positioned about a selected body or torso area in extended position with monitor 72 positioned adjacent the body. The extended position allows the elastic warp yarns, which are attempting to contract, to secure the fabric carrying the monitor in a fixed position with the body while still allowing the fabric to expand and contract due to body movement. Monitor 72, which is of known construction and forms no part of the invention, acts to detect signals sent or emitted by the body. These signals are then transmitted to a distant receiver using the conducive yarns as antenna. The monitor may send the signals as received or it may compute the signals into data which are then sent to the distant receiver.

While a preferred embodiment of the invention has been described using specific terms, such description is for illustrative purposes only, and it is to be understood that changes and variations may be made without departing from the spirit or scope of the following claims.

What is claimed is:

1. An elastic multi-ply woven fabric stretchable from a retracted position into a plurality of elongated positions for use in a physiological sensing system comprising:
   a plurality of upper and lower elastic warp yarns arranged in vertically spaced positions forming a plurality of longitudinally extending groups of laterally spaced warp yarns;
   a plurality of picks of inelastic weft yarn, first ones of said picks weaving with said upper and lower warp yarns forming upper and lower outer surfaces of cells;
   a conductive warp yarn extending longitudinally of said fabric in controlled sinusoidal configurations in each of said cells;
   second ones of said picks weaving with said conductive warp yarns between said upper and lower outer surfaces positioning each said conductive yarn in a sinusoidal configuration of said controlled sinusoidal configurations; wherein, said fabric may be extended longitudinally by about 25% from its said retracted position into various of said elongated positions causing said controlled sinusoidal configurations of said conductive yarns to be altered consistent with the degree of said extension.

2. The multi-ply woven fabric of claim 1 wherein said elastic warp yarns comprise a spandex core wrapped with an inelastic textured polyester cover.

3. The multi-ply woven fabric of claim 2 wherein said core comprises a spandex monofilament of about 420 denier.

4. The multi-ply woven fabric of claim 2 wherein said elastic wrap yarns comprises a plurality of multi-filament yarns wrapped about said core.

5. The multi-ply woven fabric of claim 1 further including a plurality of breakout points where said conductive warp yarns are caused to extend through, over and back through one of said outer surfaces to individually form connector loops over a selected length of at least one of said outer surfaces.

6. The multi-ply woven fabric of claim 5 wherein each of said connector loops are arranged in transverse rows across said at least one outer surface.

7. The multi-ply woven fabric of claim 5 wherein each of said connector loops are arranged on a single of said outer surfaces.

8. The multi-ply woven fabric of claim 5 wherein each of said break-out points are arranged at selected longitudinally spaced positions along said at least one outer surface.

9. The multi-ply woven fabric of claim 1 wherein said fabric is woven in a twelve pick repeating pattern.

10. The multi-ply woven fabric of claim 1 wherein there are at least two conductive warp yarns.

11. The multi-ply woven fabric of claim 1 wherein a single conductive yarn is located in each of said cells.

12. The multi-ply woven fabric of claim 1 wherein said conductive warp yarn comprises a wire filament core encased with wrapped textured synthetic yarns.

13. The multi-ply woven fabric of claim 12 wherein said textured yarn comprises first and second textured synthetic yarns wound in apposite directions about said wire filament.

14. The multi-ply woven fabric of claim 1 including a plurality of elastic edge warp yarns, said second ones of said picks weaving with said conductive warp yarns weaving also with said edge warn yarn, said second ones of said picks and said edge warp yarns acting to laterally stabilize said conductive warp yarns.

15. The multi-ply woven fabric of claim 1 including elastic binder warp yarns, said binder warp yarns being arranged between adjacent of said cells and weaving with said plurality of picks to separate said cells longitudinally.

16. The multi-ply woven fabric of claim 1 wherein said second ones of said picks weaving with said conductive yarns bend said conductive yarns in vertical directions creating first ones of said controlled sinusoidal configurations extending along a single plane.

17. The multi-ply woven fabric of claim 1 including elastic stuffer yams extending longitudinally of said fabric within each of said cells, on opposite sides of each of said conductive yarns, said stuffer yarns acting to stabilize said conductive yarns.

18. A method of forming a length of multi-ply elastic fabric for use in a sensing system comprising:
   causing a plurality of elastic warp yarns to be elongated along first and second vertically spaced planes in a plurality of laterally spaced positions and weaving selected picks of a plurality of picks with said selected warp yarns forming upper and lower surfaces for a plurality of cells;
   causing a plurality of conductive yarns to extend along said cells between said upper and lower surfaces;
   weaving selected other picks of said plurality of picks with said conductive warp yarns shaping said conductive warp yarns into controlled sinusoidal configurations within said cells; and
   causing said elongated elastic warp yarns to contract reducing said fabric length, causing said sinusoidal configurations of said conductive warp yarns to assume enlarged controlled sinusoidal shapes between said upper and lower surfaces; wherein
   said upper and lower surfaces formed of said elastic warp yarns maintain said controlled sinusoidal shapes of said conductive warp yarns within said cells while said fabric is positioned in numerous extended and retracted positions.

19. The method of claim 18 including causing said conductive yarns to extend through at least one of said upper and lower surfaces at selected points longitudinally of said fabric length forming loops over said outer surface.

20. A multi-ply carrier fabric for use in a physiological sensing system comprising:
   first, second and third elastic warn yarn groups each interwoven with selected ones of a plurality of picks of weft yarn through a weave pattern forming said fabric with a plurality of longitudinally extending individual cells;
   said first warn yarn group weaving with first ones of said picks forming an upper layer of said cells;
   said second warp yarn group, having less warp yarns than said first warp yarn group, weaving with second ones of said picks forming a lower layer of said cells;
   said third warn yarn group being arranged between said first and second warp yarn groups and weaving with each said pick of said plurality of picks binding said upper and lower layers together forming said cells; and,
   an inelastic conductive yarn extending within each said cell along a sinusoidal path; wherein
   said fabric, when moved between a retracted and various extended positions, allows said conductive yarns to move between varying sinusoidal shapes while being retained within said cells.

21. The fabric of claim 20 wherein said weft yarn is inelastic.

22. The fabric of claim 20 wherein at least certain of said first warp yarns are textured providing said upper layer with a plush feel.

23. The fabric of claim 20 wherein said fabric includes break-out points at selected locations longitudinally where said conductive yarns are brought above said upper layer and float for selected distances before being returned into said cells.

24. The fabric of claim 20 wherein selected of said picks of said weft yarn weave with said conductive yarns within said cells shaping said conductive yarns into fist ones of said sinusoidal shapes.

25. The fabric of claim 24 wherein said selected of said picks float through said cells at breakout points where said conductive yarns float above said upper layer.

26. The fabric of claim 20 wherein said groups of warp yarns include at least one of spandex and rubber components.

27. The fabric of claim 20 wherein said weft yarn is synthetic.

28. The fabric of claim 20 wherein said conductive yarns comprise coated wire strands.

29. The fabric of claim 28 wherein said wire strands are 28 gauge.

30. The fabric of claim 20 including stiffer warp within each cell.

* * * * *